(12) United States Patent
Lu et al.

(10) Patent No.: US 8,685,997 B2
(45) Date of Patent: Apr. 1, 2014

(54) CAMPTOTHECIN DERIVATIVES AND THEIR USE

(75) Inventors: Wei Lu, Shanghai (CN); Jian Ding, Shanghai (CN); Heyong Gao, Shanghai (CN); Liping Lin, Shanghai (CN); Yi Chen, Shanghai (CN)

(73) Assignee: Shanghai Institute of Materia Medica, Chinese Academy of Sciences, Shanghai (CN)

( * ) Notice: Subject to any disclaimer, the term of this patent is extended or adjusted under 35 U.S.C. 154(b) by 888 days.

(21) Appl. No.: 12/282,397

(22) PCT Filed: Jan. 17, 2007

(86) PCT No.: PCT/CN2007/000177
§ 371 (c)(1),
(2), (4) Date: Feb. 23, 2009

(87) PCT Pub. No.: WO2007/104214
PCT Pub. Date: Sep. 20, 2007

(65) Prior Publication Data
US 2009/0325996 A1    Dec. 31, 2009

(30) Foreign Application Priority Data
Mar. 10, 2006    (CN) .......................... 2006 1 0024590

(51) Int. Cl.
*A61K 31/44*    (2006.01)
*C07D 471/00*    (2006.01)

(52) U.S. Cl.
USPC ................................ 514/283; 546/48; 546/47

(58) Field of Classification Search
USPC ...................... 514/283; 546/48, 47
See application file for complete search history.

(56) References Cited

U.S. PATENT DOCUMENTS

| 4,604,463 A | 8/1986 | Miyasaka et al. |
| 5,674,872 A | 10/1997 | Johnson |
| 5,985,888 A * | 11/1999 | Wall et al. ..................... 514/283 |

FOREIGN PATENT DOCUMENTS

| CN | 1083817 A | 3/1994 |
| CN | 1616460 A | 5/2005 |

(Continued)

OTHER PUBLICATIONS

Kunimoto et al. "Antitumor activity of 7-ethyl-10-[1-piperidino)-1-piperidino]carbonyloxy-camptothecin, a Novel water-soluble derivative of camptothecin, against murine tumors," Cancer Research, 1987, vol. 47, pp. 5944-5947.*

(Continued)

*Primary Examiner* — Shengjun Wang
(74) *Attorney, Agent, or Firm* — Baker & Hostetler LLP

(57) ABSTRACT

New camptothecin derivatives with the following structure of the formula (I), their use and the pharmaceutical compositions containing the same. The compounds of the present invention have good anti-tumor activities and good solubility in water, and can be used in development of medicines.

6 Claims, 2 Drawing Sheets

(56) References Cited

FOREIGN PATENT DOCUMENTS

| | | |
|---|---|---|
| CN | 1673225 A | 9/2005 |
| CN | 1704416 A | 12/2005 |
| JP | S6019790 A | 1/1985 |
| JP | H01186893 A | 7/1989 |
| RU | 2165935 C2 | 4/2001 |
| WO | 2005044821 A1 | 5/2005 |

OTHER PUBLICATIONS

Dallavalle et al. "Perspectives in camptothecin development," Expert Opinion ther. Patents, 2002, vol. 12, No. 6, pp. 837-844.*

Lavergne et al. "Homocamptothecins: Synthesis and Antitumor Actvity of Novel E-Ring-Modified Camptothecin Analogs" Journal of Medicinal Chemistry, American Chemical Society, vol. 41, No. 1, Jan. 1, 1998, pp. 5410-5419, XP002242722.

Kingsbury et al. "Synthesis of Water Soluble (Aminoalkyl) Camptothecin Analogues: Inhibition of Topoisomerase I and Antitumor Activity", Journal of Medicinal Chemistry, American Chemical Society, vol. 34, No. 1, Jan. 1, 1991, pp. 98-107, XP002013003.

Journal of the American Chemical Society, vol. 88, 1966, pp. 3888-3890.

Sawada et al., "Chemical Modification of an Antitumor Alkaloid Camptothecin" Synthesis and Antitumor Activity of 7-C-Substituted Camptothecins; Chem. Pharm. Bull. 39(10) 2574-2580—1991 vol. 39, No. 10.

Yang et al., Japan Institute of Sichuan antibiotics I Industry, Sichuan 610051—Article ID 1009-5519 (2003) 08-097708 CLC; R9 Document code. pp. 977-978.

* cited by examiner (A)  (B)

CAMPTOTHECIN DERIVATIVES AND THEIR USE

CROSS-REFERENCE TO RELATED APPLICATIONS

This application is the National Stage of International Application No. PCT/CN2006/000177 filed Jan. 17, 2007, which claims the benefit of Chinese Application No. CN200610024590.7 filed Mar. 10, 2006, the entire disclosures of which are incorporated herein by reference.

TECHNICAL FIELD

The present invention relates to the field of medicinal chemistry, specifically to new camptothecin derivatives that have antitumor activities and are soluble in water, their uses and the pharmaceutical compositions containing the same derivatives.

TECHNICAL BACKGROUND

Camptothecin (abbreviated as CPT hereinafter, J. Am. Chem. Soc., 1966, 88, 3888), which was extracted and isolated from camptotheca acuminata by Wall et al. for the first time, is a pyrrole[3,4-b]quinoline alkaloid with the structure of

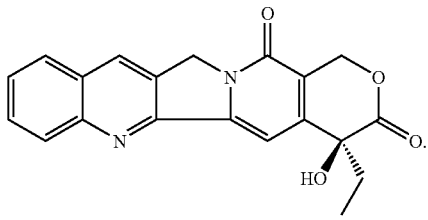 [SMILES: CC[C@@]1(O)C(=O)OCc2c1cc1n(c2=O)Cc2cc3ccccc3nc2-1]

It is a pentacyclic structure with an S-type chiral center at the 20-position on Ring E and a lactone structure near the chiral center. Although camptothecin has certain therapeutic effect on gastric cancer, rectal cancer and the like, its clinical research is limited because of its poor solubility in water and toxic side effect.

An intensive research has been made on the CPT molecular structure modifications to obtain CPT derivatives with higher activity and lower toxicity. Accordingly, a large number of CPT compounds with good effects have been synthesized. Meanwhile, it has been found that the antitumor activity can be enhanced by introducing a suitable group at the 9-position of 10-hydroxy camptothecin. For example, Topotecan commercially available at present is such a compound.

Unlike common inorganic bases and organic bases, although CPT compounds are alkaloids, their salts have poor water-solubility. Generally, there are two schemes used to solve the water solubility problem. One is to introduce a water-soluble group which can be salified, such as amino groups, into the CPT compounds, and Topotecan is such an example. The other is to introduce a provisional water-soluble group which can be dissociated in vivo into the CPT compounds, and Irinotecan (compound 4, CPT-11), a water-soluble CPT drug, is such an example.

During screening for antitumor drugs, surprisingly, the present inventors have found that the compounds obtained by introducing lower alkyl to the 9-position of 10-hydroxy camptothecin (as represented by the following formula II, wherein $R_1$ is H, $C_1$-$C_4$ alkyl, $C_1$-$C_4$ branched alkyl, or $C_1$-$C_4$ alkyl substituted by hydroxy and/or amino group) have excellent antitumor activities. Among these compounds, some have excellent therapeutic effects on solid tumor xenografts in tumor-bearing nude mice and higher therapeutic indices, thereby indicating the prospect of these compounds for further development as antitumor drugs.

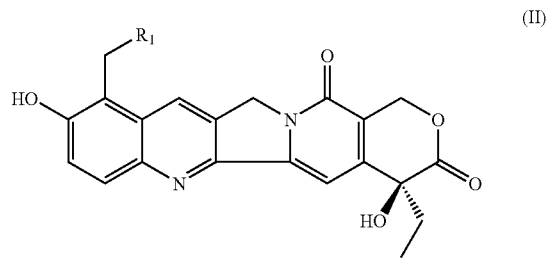

However, the compounds represented by formula II also have the problem of poor solubility in water.

DISCLOSURE OF THE INVENTION

Therefore, an object of the present invention is to provide new camptothecin derivatives with high antitumor activity and good solubility in water, based on the compounds represented by the above formula II.

Another object of the present invention is to provide pharmaceutical compositions comprising the above camptothecin derivatives.

Still another object of the present invention is to provide uses of the above camptothecin derivatives for preparing a medicament for tumor treatment.

Still further object of the present invention is to provide uses of the above pharmaceutical compositions for preparing a medicament for tumor treatment.

The present invention provides the compounds with the structure represented by the following formula I, their isomers, enantiomers or pharmaceutically acceptable salts.

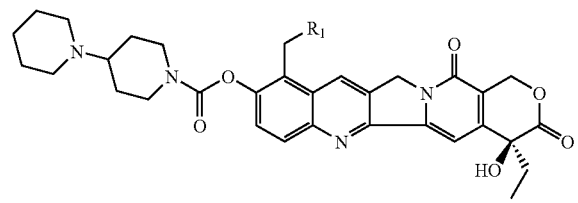

Wherein $R_1$ is H, C1-C4 alkyl, C1-C4 branched alkyl, allyl, vinyl, hydroxy, amino, C1-C4 alkyl substituted by hydroxy and/or amino group. In particular, $R_1$ may be a H; methyl, ethyl, propyl, vinyl, allyl, butyl, and their possible isomers, for example isopropyl, isobutyl; and hydroxy, hydroxymethyl, hydroxyethyl, hydroxypropyl, amino, aminomethyl, amino ethyl, aminopropyl and the like.

The examples of the said pharmaceutically acceptable salts are salts which are formed of the basic amine group of the piperidyl group introduced at the 10-hydroxy group and pharmaceutically acceptable inorganic acid or organic acid, and these salts can make the drugs soluble in water. As an example, the inorganic or organic acids can be hydrochloric acid, sulphuric acid, phosphoric acid, acetic acid, trifluoroacetic acid or trifluoromethanesulfonic acid.

Preferably, the compounds of the present invention are as follows.

10-((4'-piperidylpiperidine)carbonyloxy)-9-methylcamptothecin;
10-((4'-piperidylpiperidine)carbonyloxy)-9-ethylcamptothecin;
10-((4'-piperidylpiperidine)carbonyloxy)-9-propylcamptothecin;
10-((4'-piperidylpiperidine)carbonyloxy)-9-allylcamptothecin;
10-((4'-piperidylpiperidine)carbonyloxy)-9-isopropylcamptothecin;

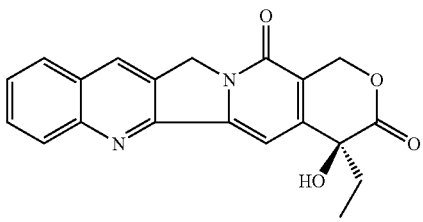 [SMILES: CC[C@@]1(O)C(=O)OCc2c1cc1n(c2=O)Cc2cc3ccccc3nc2-1]

is reacted with phosgene or solid phosgene to obtain an acyl chloride compound 6 at first, and then the obtained acyl chloride compound 6 is reacted with piperidylpiperidine (compound 7) to obtain the objective product.

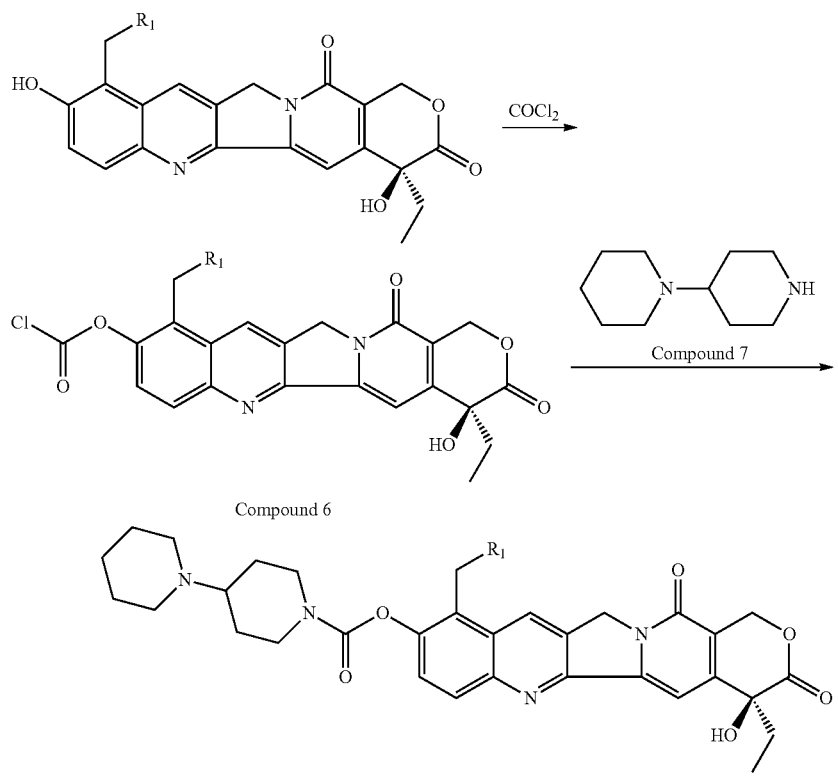

10-((4'-piperidylpiperidine)carbonyloxy)-9-n-butylcamptothecin;
10-((4'-piperidylpiperidine)carbonyloxy)-9-isobutylcamptothecin;
10-((4'-piperidylpiperidine)carbonyloxy)-9-hydroxymethylcamptothecin;
10-((4'-piperidylpiperidine)carbonyloxy)-9-hydroxyethylcamptothecin; or
10-((4'-piperidylpiperidine)carbonyloxy)-9-aminomethylcamptothecin.

The compounds of the present invention can be synthesized by the same method as that of synthesizing Irinotecan as reported in the prior art. These methods have been reported in many references (e.g. Chem. Pharm. Bull, 1991, 39, 2574).

The following two schemes illustrate the specific synthetic methods. In Scheme 1, pyrrole[3,4-b]quinoline alkaloid of the formula In Scheme 2, piperidylpiperidine is reacted with phosgene or solid phosgene to obtain an chloroformic acid amide compound 8 at first, and then the obtained chloroformic acid amide compound 8 is reacted with pyrrole[3,4-b]quinoline alkaloid in scheme 1 to obtain the objective product.

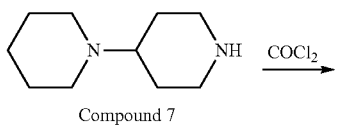

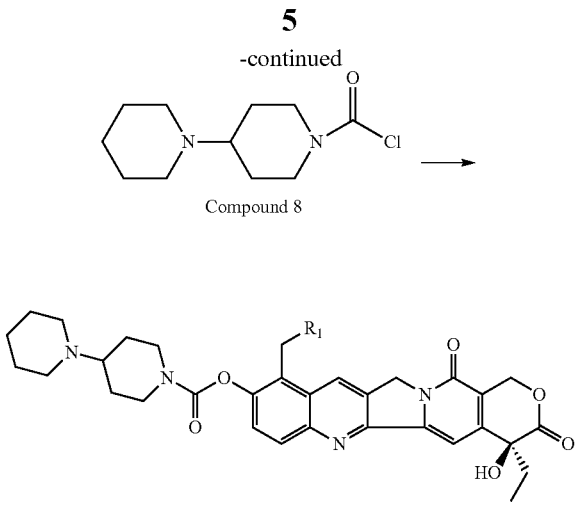

-continued

Compound 8

Both of the above schemes use the common organic synthetic reactions. Referring to the related documents on synthetic reaction, an ordinary skilled person can carry out these reactions. For brevity, the detailed description is omitted herein.

The pharmaceutically acceptable salts of the compounds of the present invention can be prepared by the conventional methods. For brevity, the detailed description is omitted herein. It is possible to form water-soluble salts according to the chemical property of the compounds of the present invention.

The present invention also provides a pharmaceutical composition comprising a therapeutically effective amount of the above compound and a conventional pharmaceutical adjuvant. The "effective amount" is the amount of the compound that is enough to improve the disease condition and does not produce severe side effects. The safe and effective amount of the compound depends on the specific conditions such as age, body weight of the subject, therapeutic indication, administration route, course of treatment, any other related therapy and the like. The said pharmaceutical adjuvant includes pharmaceutically acceptable carriers, and the "pharmaceutically acceptable carrier" means one or more compatible solid or liquid filler(s) or excipient(s) which is/are suitable for human beings and must have enough purity and enough low toxicity. The "compatibility" herein means each component of the composition can be blended one another while the pharmacodynamic action of the compound cannot be decreased obviously. Some examples of the pharmaceutically acceptable carriers are saccharide (such as glucose, sucrose, lactose, etc.), starch (such as corn starch, potato starch, etc.), cellulose and its derivatives (such as sodium carboxymethycellulose, sodium ethylcellulose, cellulose acetate, microcrystalline cellulose, etc.), acrylic resins, sodium polyacrylate, polyvidone, polyethylene glycol, polyoxyethylene monostearate, gelatin, silica gel, talc, stearic acid, magnesium stearate, calcium sulfate, vegetable oil (such as soybean oil, sesame oil, peanut oil, olive oil, etc.). It also can be emulsifier (such as Tween®), wetting agent (such as sodium dodecylsulfate), plasticizer (such as dibutyl sebacate), coloring agent, flavouring agent, stabilizer, preservative, nonpyrogenic water and the like. The choice of the carrier used in the composition of the present invention depends on the administration mode of the compound, and a person skilled in the art can select the carrier which is suitable for specific administration mode according to the prior art.

The present invention also provides the dosage forms of the above pharmaceutical composition. The dosage form may be suitable for oral administration, intravenous injection, intramuscular injection and the like, such as powder, tablet, capsule, etc.

The compounds of the present invention have anti-tumor activity, so the compounds of the present invention and the pharmaceutical composition containing the compounds may be used to prepare medicaments for tumor treatment, and further to treat tumors, and also can be used as the intervention therapy of the tumors.

The compounds of the present invention have good anti-tumor activity and solubility in water. The compounds have excellent prospect in drug development.

EMBODIMENT OF THE INVENTION

Preparation Examples

Preparation Example 1

Figure 1:
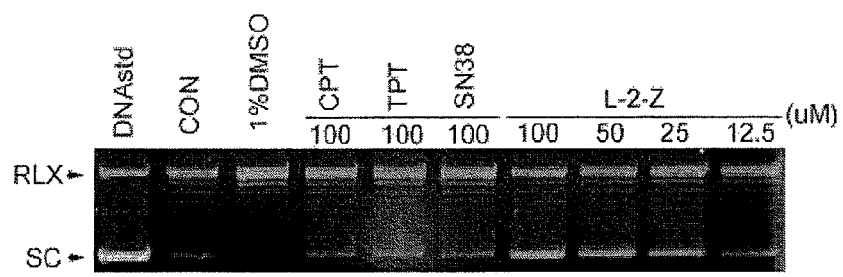
FIG. 1 shows the CPT-4 active metabolite inhibits TOPOI-mediated supercoiled pBR322 relaxation.

Preparation of 10-((4'-piperidylpiperidine)carbonyloxy)-9-allylcamptothecin(CPT-4)

One gram (1.25 equivalent weight) of piperidylpiperidine chloroformic acid amide (compound 8) was dissolved in 70 mL of dichloromethane, 10-hydroxy-9-allylcamptothecin (1 g, 1 equivalent weight) was dissolved in 70 mL of anhydrous pyridine, and then the above dichloromethane solution was added into the anhydrous pyridine solution under cooling condition. After the reaction was completed, the solvent was evaporated under reduced pressure. The residue was subjected to silica gel column chromatography, and 1.25 g of CPT-4 yellow solid was obtained. $^1$HNMR (DMSO-$d_6$) (ppm): 1.01 (3H, t), 1.58~1.90 (10H, m), 1.80~1.99 (2H, m), 2.89 (4H, b), 3.09 (1H, b), 3.71 (2H, d), 4.45 (2H, dd), 4.94 (1H, dd), 5.11 (1H, dd), 5.14 (2H, s), 5.15 (1H, d), 5.66 (1H, d), 6.00 (1H, m), 7.47 (1H, d), 7.65 (1H, s), 8.11 (1H, d), 8.51 (1H, s).

Preparation Example 2

Preparation of 10-((4'-piperidylpiperidine)carbonyloxy)-9-ethylcamptothecin(CPT-2)

Zero point nine five gram (1.25 equivalent weight) of piperidylpiperidine chloroformic acid amide (compound 8) was dissolved in 70 mL of dichloromethane, 10-hydroxy-9-ethylcamptothecin (1 g, 1 equivalent weight) was dissolved in 70 mL of anhydrous pyridine, and the above dichloromethane solution was added into the anhydrous pyridine solution under cooling condition. After the reaction was completed, the solvent was evaporated under reduced pressure. The residue was subjected to silica gel column chromatography, and 1.24 g of CPT-2 yellow solid was obtained. $^1$HNMR (DMSO-$d_6$) (ppm): 1.01 (3H, t), 1.20 (3H, t), 1.58~1.90 (2H, m), 1.80~1.99 (2H, m), 2.89 (4H, b), 3.09 (1H, b), 3.21 (2H, q), 4.45 (2H, dd), 5.14 (2H, s), 5.15 (1H, d), 5.66 (1H, d), 6.00 (1H, m), 7.47 (1H, d), 7.65 (1H, s), 8.11 (1H, d), 8.67 (1H, s).

Preparation Example 3

Preparation of 10-((4'-piperidylpiperidine)carbonyloxy)-9-propylcamptothecin(CPT-3)

One gram (1.25 equivalent weight) of piperidylpiperidine chloroformic acid amide (compound 8) was dissolved in 70 mL of dichloromethane, 10-hydroxy-9-propylcamptothecin (1 g, 1 equivalent weight) was dissolved in 70 mL of anhydrous pyridine, and the above dichloromethane solution was added into the anhydrous pyridine solution under cooling condition. After the reaction was completed, the solvent was evaporated under reduced pressure. The residue was subjected to silica gel column chromatography, and 1.17 g of CPT-3 yellow solid was obtained. $^1$HNMR (DMSO-$d_6$) (ppm): 1.01 (3H, t), 1.12 (3H, t), 1.59 (2H, m), 1.82~1.90 (2H, m), 1.80~1.99 (2H, m), 2.89 (4H, b), 3.09, 3.22 (2H, t), (1H, b), 4.45 (2H, dd), 5.14 (2H, s), 5.15 (1H, d), 5.66 (1H, d), 6.00 (1H, m), 7.47 (1H, d), 7.65 (1H, s), 8.11 (1H, d), 8.51 (1H, s).
Experimental Examples The following pharmacological tests were performed by using the above prepared compound CPT-4 of the present invention.

Experimental Example 1

Inhibit Ion of TOPO I in a Cell-Free System

TOPO I-mediated supercoiled pBR322 relaxation assays were used to test the effect of the CPT-4 active metabolite on TOPO I enzymatic activity. In this cell-free system (FIG. 1, wherein, RLX: relaxed DNA; SC: supercoiling DNA), the CPT-4 active metabolite could inhibit the TOPO I-mediated supercoiled DNA relaxation. The inhibition of the CPT-4 active metabolite was stronger than that of CPT TPT (Topotecan) and SN38 (the active metabolite of Irinotecan) at the same concentrations.

Experimental Example 2

In Vitro Anti-Tumor Activity

1. Sulfonyl rhodamine B (SRB) protein staining assays were used to detect the inhibition of tumor cell proliferation of the compound. The results showed the CPT-4 active metabolite could effectively inhibit the proliferation of the tumor cells at lower concentrations (table 1), Its mean value of $IC_{50}$ (115.2 DM) to thirteen tumor cell lines was lower than that of the control compounds TPT (378.6 nM), SN38 (218.5 nM) and 9-nitrocamptothecin (9-NC) (167.0 nM). Meanwhile, the compound had selectivity to tumor cell lines originated from different tissues. Wherein the lung cancer, rectal cancer and breast cancer cell lines were sensitive to the CPT-4 active metabolite, and liver cancer, gastric cancer and ovarian cancer were less sensitive (the results were shown in Table 1).

TABLE 1

The CPT-4 active metabolite inhibited the proliferation of tumor cells

| Cell lines | IC50(mean ± SD)(nM) | | | |
| --- | --- | --- | --- | --- |
| | TPT | SN38 | 9NC | CPT-4 active metabolite |
| HL-60 | 23.28 ± 1.32 | 6.70 ± 1.26 | 20.57 ± 2.56 | 9.18 ± 0.20 |
| A549 | 28.09 ± 6.80 | 5.90 ± 1.61 | 31.95 ± 3.72 | 4.68 ± 1.32 |
| NCI-H23 | 122.14 ± 36.30 | 234.39 ± 115.95 | 70.34 ± 14.58 | 10.57 ± 1.20 |
| SGC-7901 | 488.67 ± 96.52 | 465.00 ± 75.35 | 98.00 ± 6.87 | 318.00 ± 51.39 |
| MKN-28 | 411.68 ± 188.46 | 303.48 ± 56.04 | 115.81 ± 6.48 | 57.28 ± 45.56 |
| HCT-116 | 38.02 ± 2.19 | 12.87 ± 5.40 | 13.71 ± 1.40 | 7.20 ± 2.37 |
| HCT-15 | 14.40 ± 4.41 | 6.13 ± 4.07 | 9.59 ± 0.48 | 10.40 ± 1.52 |
| BEL-7402 | 420.33 ± 79.66 | 135.63 ± 34.72 | 58.80 ± 10.65 | 313.00 ± 24.04 |
| SMMC-7721 | 1382.85 ± 171.56 | 378.70 ± 66.43 | 1380.20 ± 25.00 | 466.17 ± 107.60 |
| MCF-7 | 386.95 ± 45.61 | 72.95 ± 15.56 | 62.59 ± 19.76 | 35.41 ± 25.15 |
| MDA-MB-435 | 49.71 ± 6.05 | 3.42 ± 1.53 | 18.50 ± 6.14 | 9.89 ± 0.25 |
| MDA-MB-468 | 176.45 ± 97.46 | 95.64 ± 36.91 | 64.87 ± 29.65 | 17.28 ± 8.84 |
| HO-8910 | 1379.71 ± 44.42 | 1119.11 ± 170.95 | 226.68 ± 40.76 | 238.50 ± 161.36 |

Figure 2:
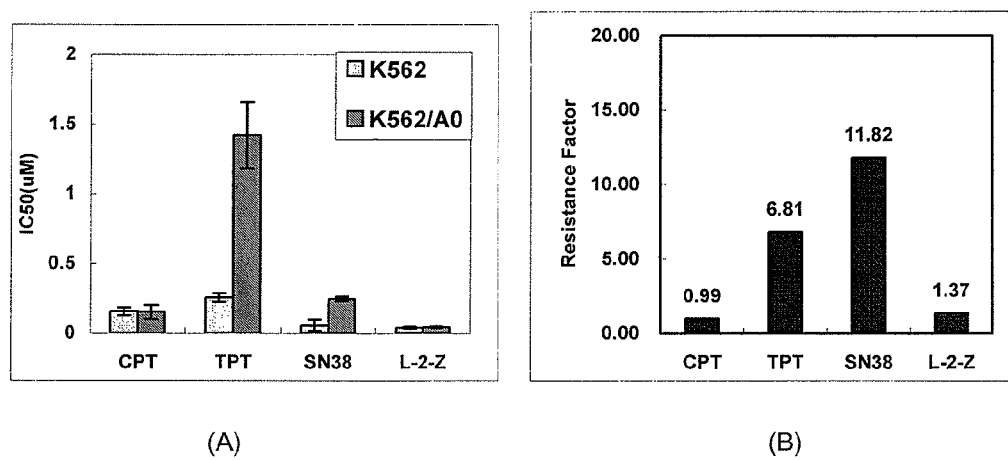
FIG. 2 shows the anti-multidrug resistance of the CPT-4 active metabolite.
Figure 3:
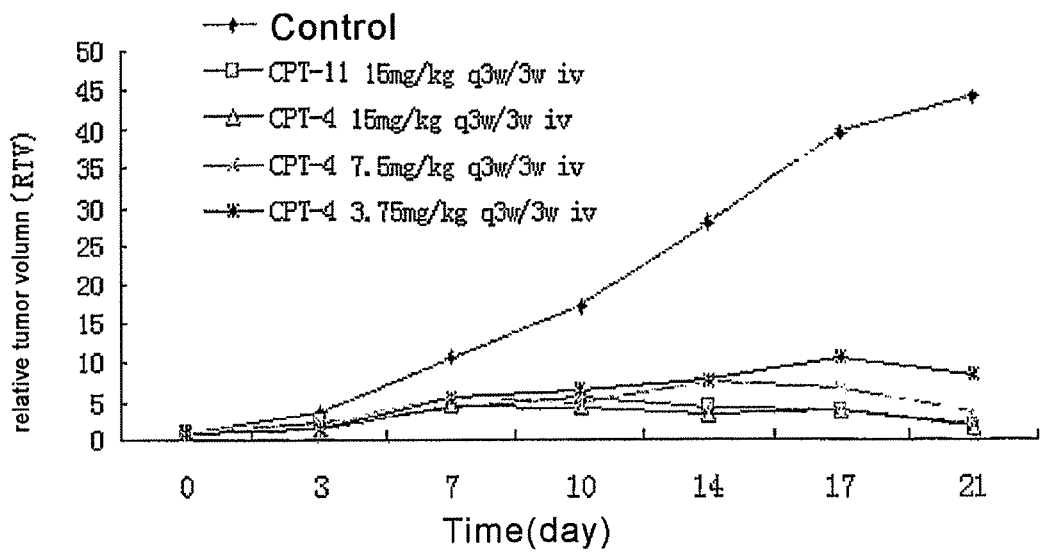
FIG. 3 shows the experimental therapeutic effect of CPT-4 on human rectal cancer HCT-116 xenografts in nude mice.
Figure 4:
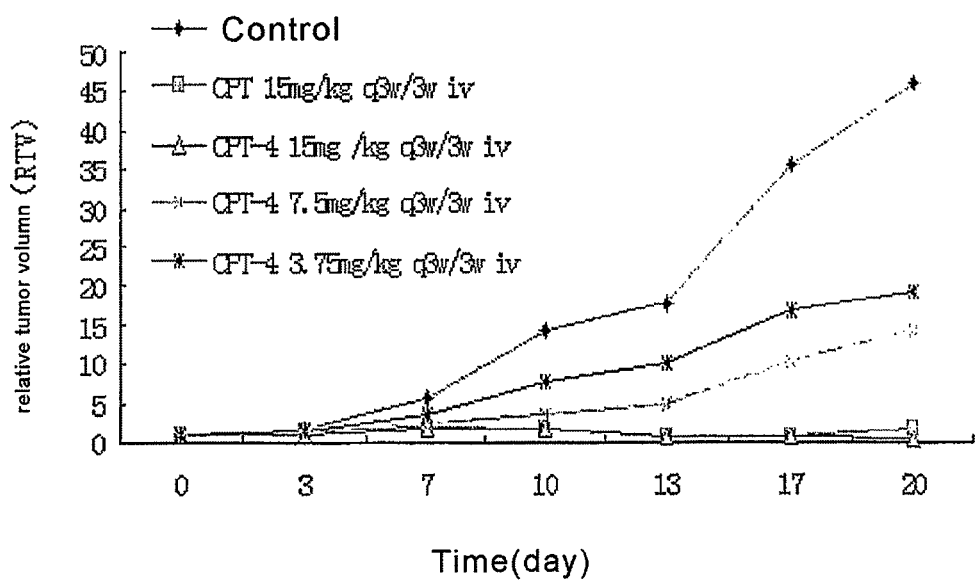
FIG. 4 shows the experimental therapeutic effect of CPT-4 on human lung cancer SPC-A4 xenografts in nude mice.

2. The multidrug resistance cell line K562/A02 and its parent K562 cell line were used to evaluate the anti-multidrug resistance of the CPT-4 active metabolite. The $IC_{50}$'s of adriamycin to K562 and K562/A02 cells were 0.493 and 69.141 μM, respectively, and Resistance Factor (RF) was 140.24. The results showed that CPT-4 active metabolite had equivalent toxicities to both cell lines, and showed obvious anti-multidrug resistance effect, and the effect was stronger than that of TPT and SN38 (the results were shown in FIG. 2, wherein (A) $IC_{50}$'s of MDR K562/A02 and its parent K562 cells; (B) Resistant Factor).

Experimental Example 3

In Vivo Anti-Tumor Activity

Human rectal cancer HCT-116 cells or human lung cancer SPC-A4 cells were inoculated into armpits of nude mice. When the volume of the tumors reached 100~200 mm$^3$, the nude mice were separated to different cages at random and CPT-4 at different concentrations or normal saline was intravenously administrated three times per week. The results showed the compound can significantly inhibit the growth of tumor xenografts, and the effect was equivalent to that of CPT-11 (water soluble CPT drug, Irinotecan). The results were shown in Table 2 and Table 3.

TABLE 2

Experimental therapeutic effect of CPT-4 on human rectal cancer HCT-116 xenografts in nude mice.

| Group | Dose | Administration mode | Number of animals | | Body weight (g) | | TV (mm$^3$) | | | T/C |
| --- | --- | --- | --- | --- | --- | --- | --- | --- | --- | --- |
| | | | At the beginning | At the end | At the beginning | At the end | $d_0$ | $d_{21}$ | RTV | (%) |
| Control | 0.2 ml per animal | i.v. | 12 | 12 | 20.0 | 20.7 | 93 ± 58 | 3360 ± 754 | 44 ± 28 | |
| CPT-11 | 15 mg/kg, q3w × 3 | i.v. | 6 | 6 | 20.7 | 18.3 | 101 ± 60 | 171 ± 86 | 1.9 ± 1.1 | 4.37 |
| CPT-4 | 15 mg/kg, q3w × 3 | i.v. | 6 | 6 | 20.3 | 17.8 | 100 ± 20 | 172 ± 51 | 1.8 ± 0.5 | 3.99 |
| CPT-4 | 7.5 mg/kg, q3w × 3 | i.v. | 6 | 6 | 19.5 | 17.2 | 94 ± 30 | 289 ± 108 | 3.8 ± 2.2 | 8.31 |
| CPT-4 | 3.75 mg/kg, q3w × 3 | i.v. | 6 | 6 | 20.2 | 17.0 | 92 ± 27 | 720 ± 75 | 8.4 ± 2.0 | 18.9 |

TABLE 3

Experimental therapeutic effect of CPT-4 on human lung cancer SPC-A4 xenografts in nude mice.

| Group | Dose | Administration mode | Number of animals | | Body weight (g) | | TV (mm$^3$) | | | T/C |
| --- | --- | --- | --- | --- | --- | --- | --- | --- | --- | --- |
| | | | At the beginning | At the end | At the beginning | At the end | $d_0$ | $d_{20}$ | RTV | (%) |
| Control | 0.2 ml per animal | i.v. | 12 | 12 | 18.2 | 22.4 | 108 ± 56 | 4361 ± 988 | 46 ± 20 | |
| CPT-11 | 15 mg/kg, q3w × 3 | i.v. | 6 | 6 | 18.2 | 18.7 | 121 ± 34 | 55 ± 39 | 0.5 ± 0.5 | 1.13 |
| CPT-4 | 15 mg/kg, q3w × 3 | i.v. | 6 | 6 | 17.3 | 17.5 | 106 ± 28 | 55 ± 99 | 0.4 ± 0.7 | 0.88 |
| CPT-4 | 7.5 mg/kg, q3w × 3 | i.v. | 6 | 6 | 17.5 | 19.3 | 108 ± 61 | 1153 ± 172 | 14 ± 5.5 | 31.4 |
| CPT-4 | 3.75 mg/kg, q3w × 3 | i.v. | 6 | 6 | 17.8 | 19.3 | 104 ± 22 | 1931 ± 533 | 19 ± 5.5 | 41.4 |

Note:
The tumor in one nude mouse in CPT-4 15 mg/kg group was completely regressed.

The invention claimed is:

1. A compound represented by the following general formula I or its pharmaceutically acceptable salt,

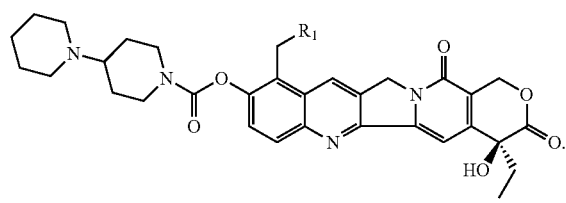

wherein R$_1$ is vinyl.

2. The compound or its pharmaceutically acceptable salt according to claim 1, wherein the said pharmaceutically acceptable salt is a salt which is formed by reaction of the said compound with hydrochloric acid, sulphuric acid, phosphoric acid, acetic acid, trifluoroacetic acid or trifluoromethanesulfonic acid.

3. A pharmaceutical composition comprising a therapeutically effective amount of the compound or its pharmaceutically acceptable salt according to claim 1 and a conventional pharmaceutical adjuvant.

4. The pharmaceutical composition according to claim 3, wherein the said pharmaceutical composition is prepared in the dosage form of oral or injection administration.

5. A method for treating tumor diseases comprising administering to a subject in need of the same compound or its pharmaceutically acceptable salt according to claim 1.

6. A method for treating tumor diseases comprising administering to a subject in need of the same pharmaceutical composition according to claim 3.

* * * * *